United States Patent [19]

Jarvik

[11] 4,226,242
[45] Oct. 7, 1980

[54] REPEATING HEMOSTATIC CLIP APPLYING INSTRUMENTS AND MULTI-CLIP CARTRIDGES THEREFOR

[75] Inventor: Robert K. Jarvik, Salt Lake City, Utah

[73] Assignee: United States Surgical Corporation, Norwalk, Conn.

[21] Appl. No.: 832,972

[22] Filed: Sep. 13, 1977

Related U.S. Application Data

[63] Continuation-in-part of Ser. No. 730,933, Oct. 8, 1976, Pat. No. 4,166,466.

[51] Int. Cl.² ............................................. A61B 17/12
[52] U.S. Cl. .................................... 128/325; 221/232
[58] Field of Search ........... 128/325, 326, 335, 334 R, 128/346, 337; 227/19; 206/339; 221/232

[56] References Cited

U.S. PATENT DOCUMENTS

| 2,242,502 | 5/1941 | Bangs | 221/232 |
| 2,310,180 | 2/1943 | Kuhnl | 221/232 |
| 2,483,379 | 9/1949 | Brell | 221/232 |
| 3,363,628 | 1/1968 | Wood | 128/337 X |
| 3,586,002 | 6/1971 | Wood | 128/337 |
| 3,604,561 | 9/1971 | Mallina et al. | 227/19 X |

*Primary Examiner*—Stanley H. Tollberg
*Attorney, Agent, or Firm*—Fleit & Jacobson

[57] ABSTRACT

A cartridge for use with a repeating hemostatic clip applying instrument. The instrument is generally shaped and operated in the manner of prior clip applying instruments. Shaped like a pair of dog-nosed pliers, the outer ends of the jaws are adapted to hold a clip which may be applied to a blood vessel with the instrument. The rearward portion of the jaws overlap and a rectangular channel is formed in one of them through which clips may be pushed by a pusher extending down the center line of the instrument. One of the jaws is adapted to receive a cartridge containing a stack of U-shaped clips which may be pushed one at a time to the distal end of the jaws by the pusher.

The cartridge is provided with a spring for urging the U-shaped stack of clips down to the pusher channel, and a clip follower for preventing misalignment of the clips in the cartridge.

26 Claims, 22 Drawing Figures

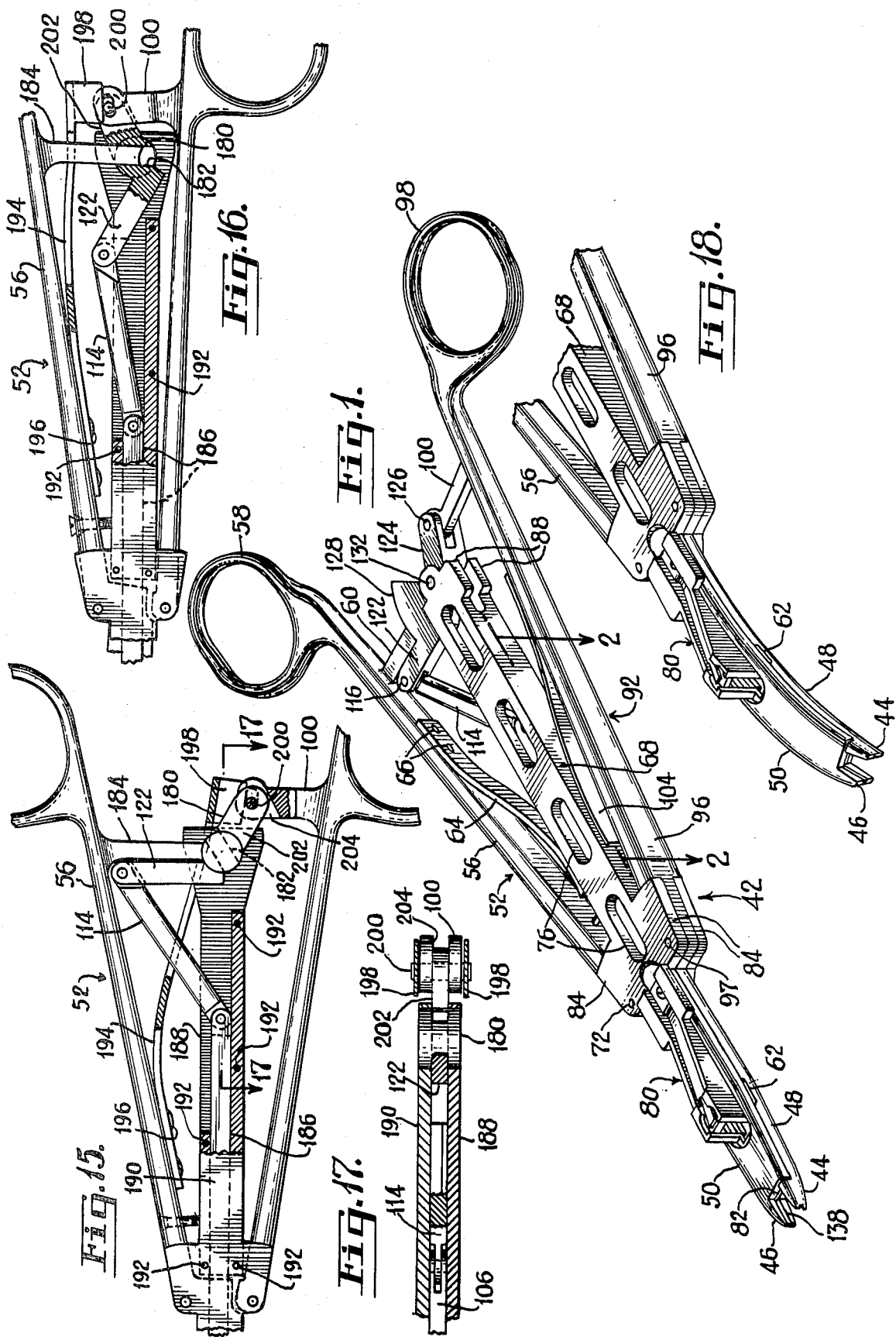

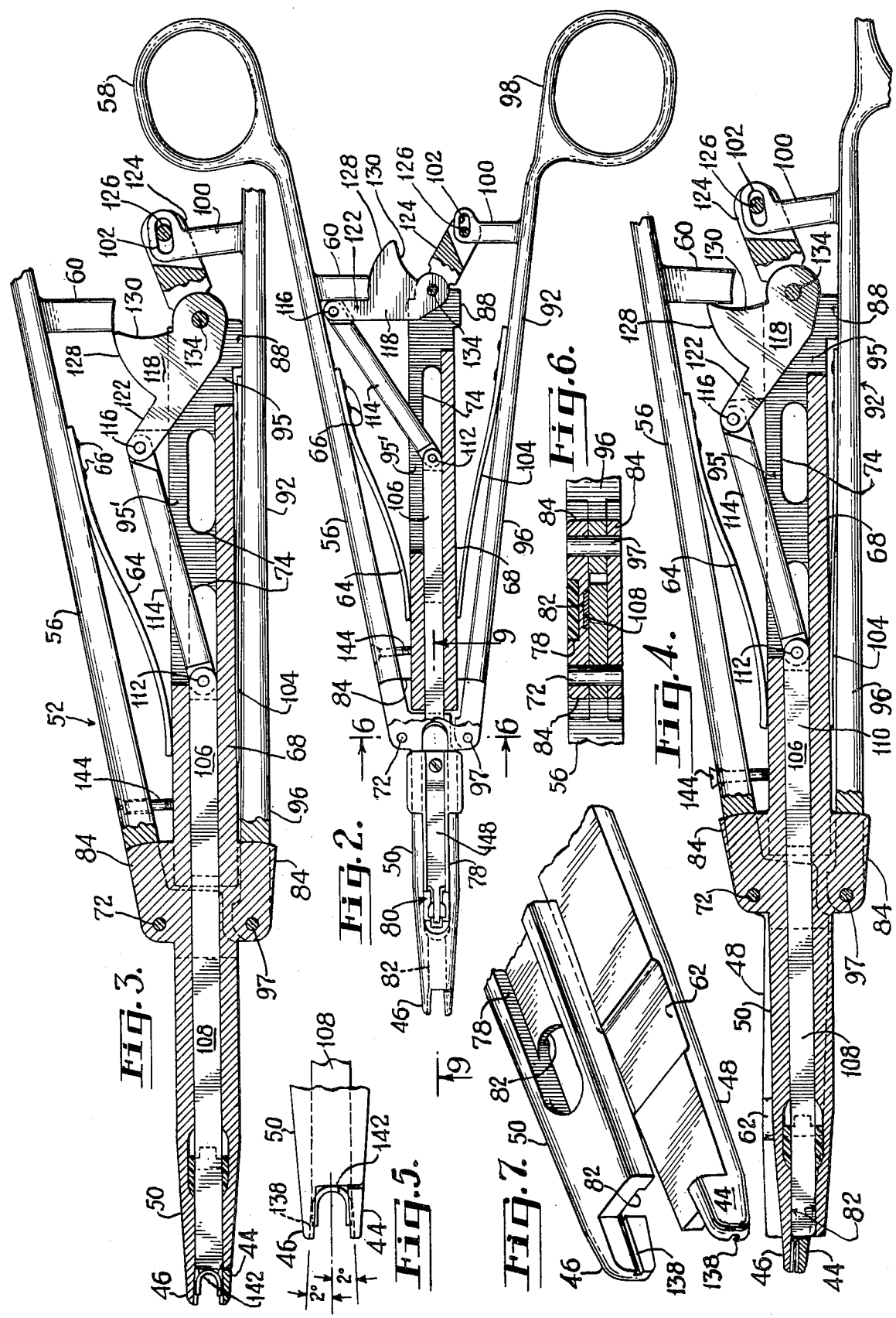

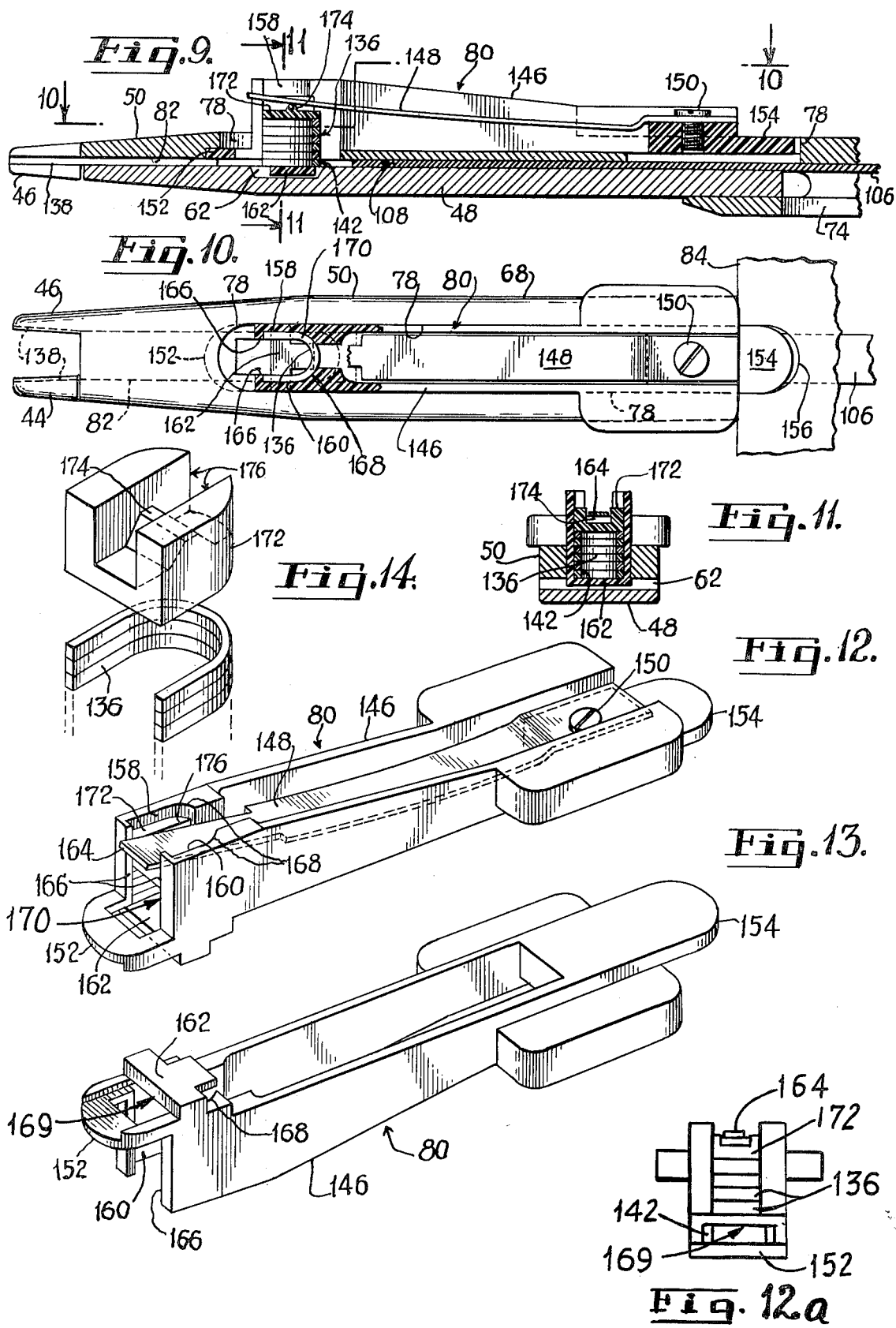

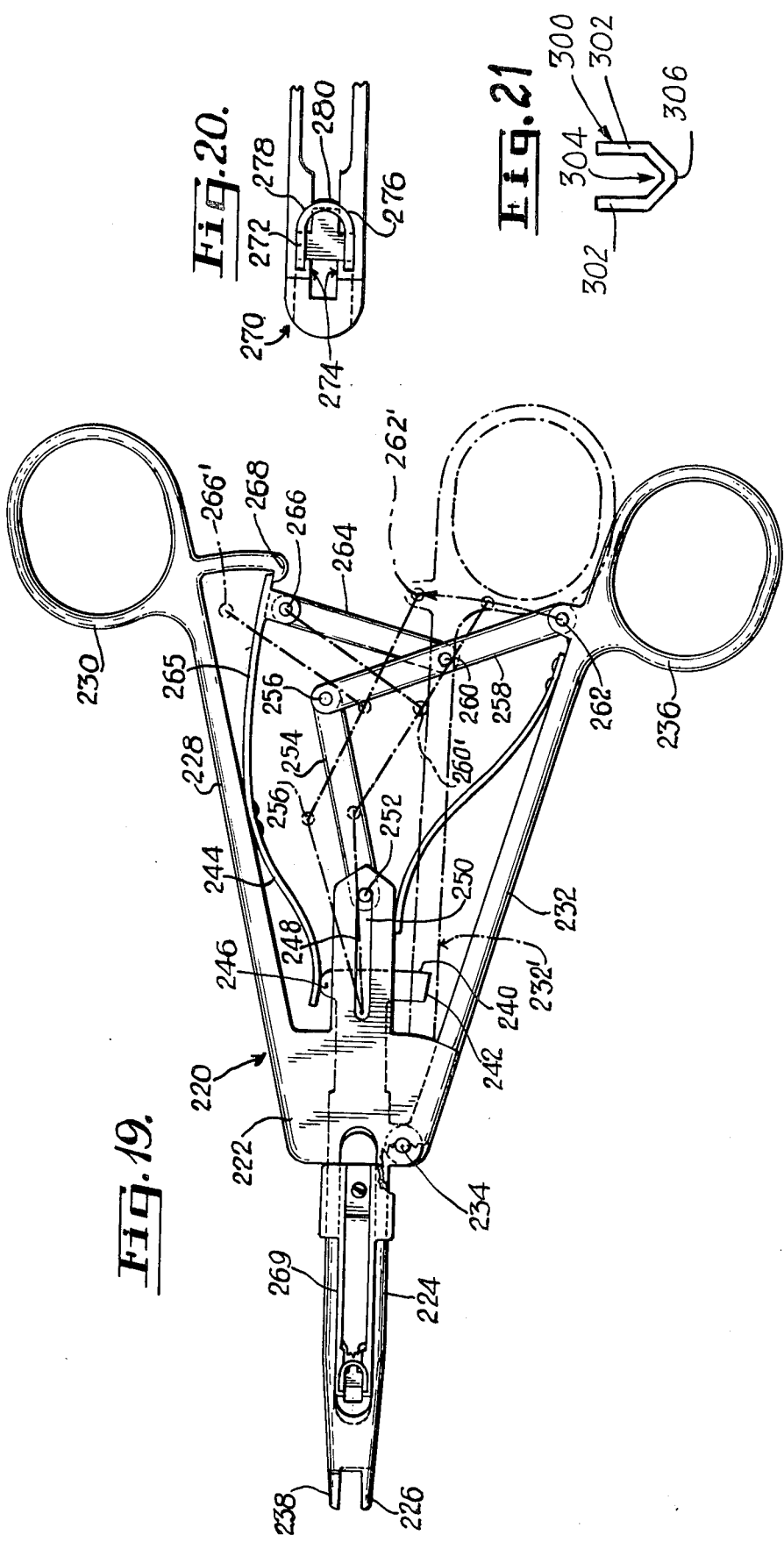

REPEATING HEMOSTATIC CLIP APPLYING INSTRUMENTS AND MULTI-CLIP CARTRIDGES THEREFOR

RELATED APPLICATIONS

This application is a Continuation-in-part of my United Stated Application, Ser. No. 730,933, filed Oct. 8, 1976, entitled "REPEATING HEMOSTATIC CLIP APPLYING INSTRUMENTS AND MULTI-CLIP CARTRIDGES THEREFOR", now U.S. Pat. No. 4,166,466.

SUMMARY OF THE INVENTION

This invention relates to repeating hemostatic clip applying instruments and multi-clip cartridges therefor. More particularly, it relates to the rapid and repeated ligation of so called bleeders in surgical procedures.

After a surgeon has made his incision, it is necessary to clamp the tissue wherever blood is being lost due to the cutting of blood vessels. The usual technique is to clamp each so-called bleeder with a hemostat (locking dog-nosed pliers) as soon after the vessel is severed as possible. This controls the loss of blood until a ligature can be tied around the vessel. As many as 20 or more bleeders may be clamped by as many hemostats in common surgical procedures before they are tied. Thus, a single operation often requires the use of a large number of hemostats. These are handed to the surgeon and his assistants, one at a time, by the scrub nurse.

The surgical field often becomes cluttered with hemostates, which interfere with the surgeon's view and hinder the convenient application of additional hemostats. However, a good surgical practice requires the application of hemostats to all bleeders before they are tied.

The tying process requires one hand to hold the hemostat and two hands to pass the suture material around the hemostat and to form the ligature by tying a knot. This procedure thus requires two people. In addition, the ligatures must be cut and the excess suture material removed from the incision. The used hemostats must be handed to the scrub nurse and be readied for reuse. Thus, this entire technique for the achievement of hemostasis requires the coordination and teamwork of at least three people. The speed with which the bleeders may be tied off is often the determining factor in the time required for the opening stages of many surgical operations.

Many instruments have been disclosed in the prior art for ligating bleeders. However, none of these have come into general use, due to inherent deficiencies. Instruments such as disclosed in U.S. Pat. Nos. 3,033,204, 3,040,747, and 3,169,526, issued to E. C. Wood; U.S. Pat. No. 2,268,755, issued to S. F. Li; and U.S. Pat. No. 1,635,602, issued to H. G. Gould et al have been designed for aiding the surgeon is applying a single pretied length of suture material to a bleeder. Other instruments, such as that disclosed in U.S. Pat. No. 2,371,082 issued to F. Vistreich are designed to apply a single collar of resilient material to a deep bleeder. However, these instruments, since they apply only one ligature at a time after which another preformed ligature must be affixed to the instrument before it can then be applied to the next bleeder, do not materially reduce the amount of time or effort required in a surgical procedure. Other more complex instruments, such as disclosed in U.S. Pat. Nos. 2,898,915 and 2,898,916, issued to K. Kammer, have been devised for automatically tying a successive plurality of ligatures from a spool of suture material. I disclosed a repeating ligature gun for applying a plurality of pretied or preformed ligatures (U.S. Pat. No. 3,687,138). However, these prior art instruments are complex, are difficult to load with the suture material, and, being complicated, are hard to disassemble and sterilize. None of the above prior art instruments have come into general use.

In order to obviate some of the above problems in the prior art, hemostatic clips have come into widespread use in surgery in recent years. In current surgical practice, these clips are used not only for occluding blood vessels but also for application to other structures such as nerves; for example, in vagotomy. A number of efforts have been made to facilitate loading of the clips into the instrument. This generally is done one at a time by a scrub nurse who then hands the instrument to the surgeon for application and receives the empty instrument back for reloading with another single clip. As the clips are small and difficult to handle, cartridges which hold the clips and then aid in loading the clips one at a time into the instrument have been developed. Since the clips are not firmly held in the instruments, they sometimes fall out during handling of the instrument by the scrub nurse and the surgeon prior to application.

What is needed is an instrument which will rapidly and repeatedly clamp and ligate bleeders; an instrument that can be operated with one hand; an instrument which does not leave any excess material, such as cut ends in the incision; an instrument which may be reloaded by means of a cartridge with a plurality of preformed ligatures repeatedly during an operation; and an instrument which is easy to disassemble and sterilize.

It is also desirable that the instrument handle as much as possible in the same manner as prior art surgical instruments such as towel clamps, hemostats, and clip appliers. Furthermore, it would be a highly desirable feature of such an instrument if it were adapted to apply a hemostatic clip which has already been accepted in surgical practice and in particular approved by the Food and Drug Administration (FDA) for retention in the human body as the provision of any other material or even shape of clip or preformed ligature may be occasioned with years of tests and delay before FDA approval may be secured.

OBJECTS OF THE INVENTION

It is therefore an object of the invention to improve the art of surgery.

Another object of the invention is to provide for rapid ligation of a plurality of bleeders.

Still another object of the invention is to provide preformed clips for facilitating the above objects.

A further object of the invention is to provide an instrument for applying a plurality of clips of the above character.

Another object of the invention is to provide an instrument of the above character which may be operated by one hand.

A further object of the invention is to provide an instrument of the above character which leaves no excess material or cut ends on the sutures in the body which have to be removed by the surgeon.

Still another object of the invention is to provide an instrument of the above character which is convenient to sterilize without disassembly.

Yet another object of the invention is to provide an instrument of the above character which does not require lubrication.

Still another object of the invention is to provide an instrument of the above character employing a replaceable cartridge or carrier for a plurality of preformed clips of the above character.

A further object of the invention is to provide a cartridge of the above character which is disposable.

A still further object of the invention is to provide an instrument of the above character which can affix clips to bleeders with varying tension according to the size of the vessel and type of tissue in which it occurs.

Another object of the present invention is to provide an automatic repeating clip applying instrument which will obviate the need for reloading prior to each clip application, hold the clips securely during handling so they cannot fall out, and speed surgical procedures.

It is a further object of the invention to provide a repeating instrument which has substantially the same form as present single clip applying instruments and which operates essentially the same as single clip instruments do during clip application; that is, which crushes a clip flat between two jaws when two ring handles are squeezed together thus providing the same "feel" as hemostats and clip appliers of the prior art.

To facilitate reloading of the repeating instrument, it is also an object of the present invention to provide a disposable cartridge containing a plurality of clips, which may be simply and quickly affixed to and removed from the instrument.

Still a further object is to provide an instrument with an elongated tip having delicate jaws to permit unobstructed visibility of the clip applying jaws as the clip is applied to tissue even in deep and restricted areas. To accomplish this, it is an object of the invention to provide a small and streamlined cartridge which is located remote from the tip.

Another object of the invention is to provide an instrument of the above character which is adapted to apply hemostatic ligating clips which have already been accepted in surgical practice and by the Food and Drug Administration.

A further object of the invention is to provide an instrument of the above character which is highly reliable and formed of very few moving parts.

Still another object of the invention is to provide an instrument, cartridge and clips of the above character which may be mass produced at low cost, are convenient to use, and require little or no servicing.

Other objects of the invention will in part be obvious and will in part appear hereinafter.

The invention accordingly comprises articles of manufacture possessing the features, properties and the relations of elements which will be exemplified in the articles hereinafter described, and apparatus comprising the features of construction, combinations of elements and arrangements of parts which will be exemplified in the constructions hereinafter set forth. The scope of the invention is indicated in the claims.

THE DRAWINGS

For a fuller understanding of the nature and objects of the invention, reference should be had to the following detailed description taken in connection with the accompanying drawings in which:

FIG. 1. is a top perspective view of a repeating hemostatic clip applying instrument and multi-clip cartridge therefor assembled and ready for operation.

FIG. 2 is a top view of the instrument shown in FIG. 1 in partial cross section along the plane 2—2 of FIG. 1.

FIG. 3 is an enlarged top view, partially cut away, of the instrument shown in FIG. 1 with the cross section of FIG. 2 extended and the instrument partially actuated to move a clip from the cartridge to the clip applying jaws.

FIG. 4 is an enlarged top view, partially in cross section, similar to FIG. 3 showing the instrument fully actuated to close the clip between the jaws.

FIG. 5 is an enlarged cut away view showing a detail of the jaws.

FIG. 6 is a cross-sectional view, partially cut away, taken along the line 6—6 of FIG. 2.

FIG. 7 is an enlarged exploded perspective cut away view of the clip applying jaws and a portion of the cartridge mount.

FIG. 9 is an enlarged cross-sectional cut away view taken along the plane 9—9 of FIG. 2.

FIG. 10 is a top cross-sectional cut away view taken along the line 10—10 of FIG. 9.

FIG. 11 is a cross-sectional view taken along the line 11—11 of FIG. 9.

FIG. 12 is an enlarged top perspective view of the cartridge of the invention shown in FIG. 1.

FIG. 12A is an end plan view of the cartridge shown in FIG. 12.

FIG. 13 is an enlarged perspective bottom view similar to FIG. 12.

FIG. 14 is an enlarged perspective diagrammatic top view of the clips and clip follower of the cartridge of FIG. 1.

FIG. 15 is a partial cross-sectional top view, partially cut away, similar to FIG. 2, of an alternative embodiment of the invention having a different clip advancing mechanism.

FIG. 16 is a top view partially in cross-section and partially cut away similar to FIG. 15 showing the alternative embodiment with the clip advance mechanism fully advanced.

FIG. 17 is a partial cross-sectional view partially cut away taken along the line 17—17 of FIG. 15.

FIG. 18 is a top perspective view similar to FIG. 1, partially cut away, of an alternative embodiment of the invention having curved jaws for improved handling and visibility.

FIG. 19 is a top plan view of another alternative embodiment of the invention having a single pivot and a floating bell crank pusher actuating mechanism.

FIG. 20 is a top plan diagrammatic view of an alternative form of clip cartridge.

FIG. 21 is a top plan view of a U-shaped clip having a V-shaped connecting section.

The same reference characters refer to the same elements throughout the several views of the drawings.

GENERAL DESCRIPTION

Figure 8:
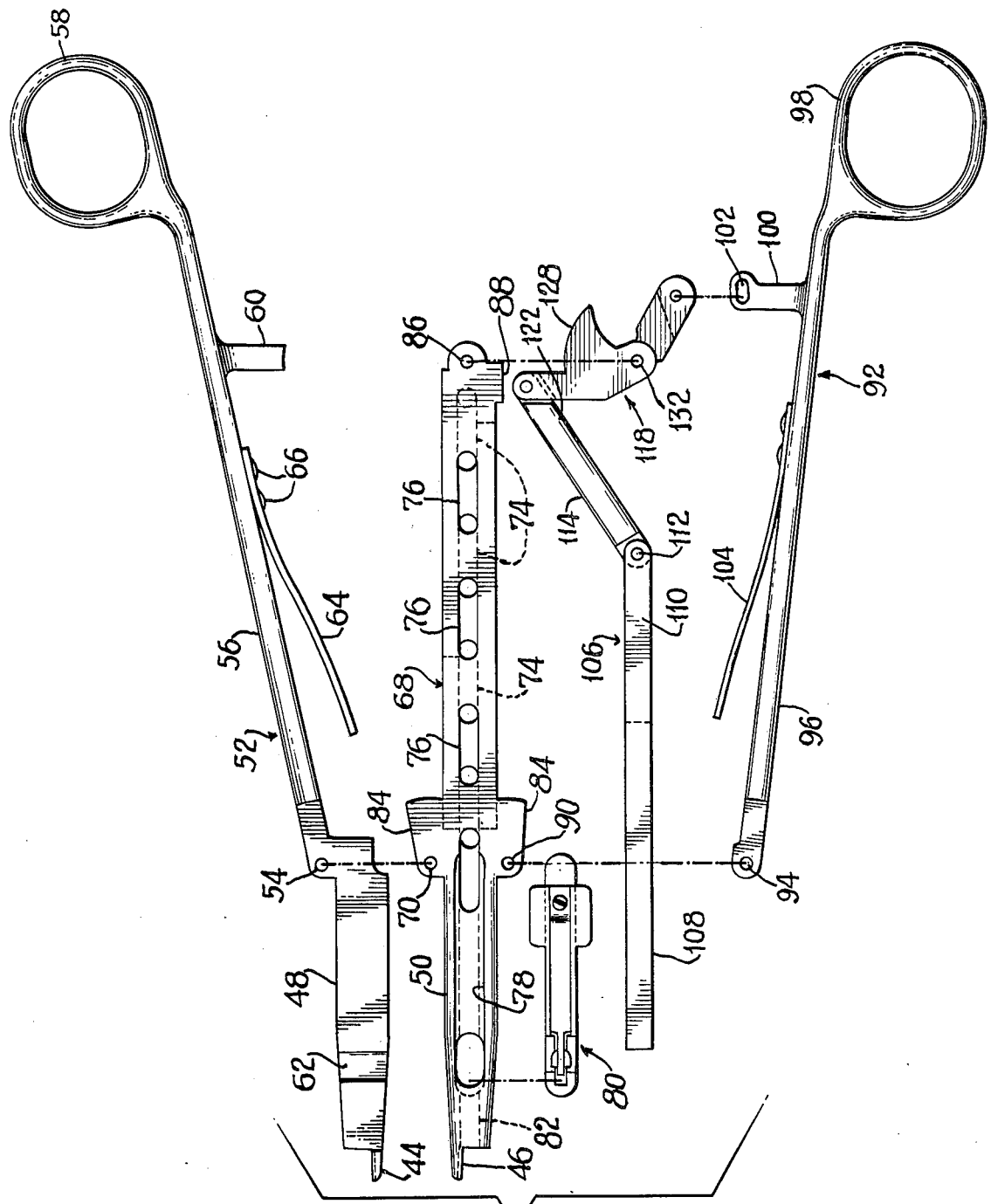
FIG. 8 is an exploded diagrammatic view showing the small number of basic parts of the instrument of FIG. 1.

In general, the present invention is similar in function to existing single clip applying instruments such as disclosed in U.S. Pat. No. 3,713,533 in that with one actuation of the instrument, one clip is applied to tissue by being crushed thereabout by a pair of jaws. The clips are preferably also of substantially the same material size and shape when closed about the tissue as the formed clips disclosed in that patent. The instrument of this invention is so designed that in its preferred embodiment it is substantially similar in shape to present single clip applying instruments which are, in fact, designed much like numerous types of hemostats and other surgical clamps, having two ring handles and a generally elongated form which permits controlled handling and good visibility at the tip.

The present invention differs from single clip applying instruments in that a disposable cartridge is provided which holds a plurality of clips and feeds them to the instrument one at a time. Other instruments have been patented for repeatedly applying surgical clips or ligatures such as disclosed in U.S. Pat. Nos. 2,277,139, 2,968,041, 3,082,426, 3,844,289, 3,638,847, and my Patent No. 3,841,521. However, although the need for a repeating hemostatic clip applying instrument has been recognized for decades, none is presently in the market or in clinical use.

Deficiencies in prior art repeating instruments which have led to their nonuse in clinical practice may be categorized as: overly complex instruments with a very large number of parts; instruments which obscure the physicians' field of view; gun type instruments which meet great resistance on the part of surgeons used to ring-handled plier type instruments; instruments with a great many small moving interfaces between parts which make them subject to frictional failure, extremely difficult to sterilize without dissassembly, and extremely difficult to disassemble and re-assemble for good sterilization practice; lack of simple replaceable cartridges; operation which requires pulling of tissue into the instrument; and complex cartridge mechanisms which lead to prohibitive cartridge costs.

The present invention recognizes that optimal visibility to the tip, incorporation of an inexpensive multiple clip containing cartridge which can be rapidly changed, and completely automatic one hand operation, preferably with a ring handle configuration, are crucial if the instrument is to be clinically useful.

A new principle unique to all clip applying instruments is employed. A disposable cartridge, removably mounted on the instrument, holds a plurality of clips in alignment with a channel on the instrument. The instrument then removes the clips, one at a time, from the cartridge and feeds them through the channel to the jaws for application to the tissue. This principle of having the cartridge feed the clips to a position on the instrument remote from the jaws and then having the instrument feed each clip to the jaws permits the cartridge to be placed remote from the jaws, out of the line of visibility. It also permits the simplest possible construction of the jaws, that is, of only two pieces, which further aids visibility.

The instrument of this invention thus has a pair of clip applying jaws with a channel leading thereto from a remote position where a cartridge containing a plurality of clips may be removably affixed. It, in addition, has a clip feed mechanism and appropriate sequencing and spring return means so that, in operation, when a pair of ring handles are squeezed together, the forwardmost clip is removed from the cartridge, fed to the jaws and clamped about isssue positioned therebetween, and, upon release, the instrument returns to a position ready to repeat.

The instrument is basically comprised of four main portions: (1) a first pivoted member comprising a ring handle with a wide distal portion terminating in one jaw member; (2) a second pivotal member having a wide distal portion terminating in the other jaw member; (3) a clip pushing mechanism; and (4) an elongated ring handle. One of the distal portions is provided with a channel for a pusher to push the hemostatic clips to the jaws. This distal portion also has a cartridge receiving portion. The other distal portion acts as a cover for the channel. A linkage is provided between the ring handles and the clip pushing mechanism for pushing the clip out of the cartridge, forward to the jaws and then allowing the jaws to close. This is accomplished in two embodiments of the invention by providing a rotating bell crank on a proximal extension of the pusher channel member.

The bell cranks each have a cam which is engaged by an extension on one of the ring handles and is operated by an extension on the other ring handle to rotate when the handles are first closed to operate the push member. The cam has a cut away portion into which the extension on the opposite ring handle then falls to allow the handle to close and close the jaws.

In another embodiment of the invention, the bell crank is free floating and is connected by its center pivot to one ring handle and at one of its outer pivots to the other ring handle, and at the other outer pivot to a link connected to the pusher. This free floating bell crank linkage, by its geometry, causes the pusher to be operated against the force of a weak spring. Thereafter the ring handle to which no jaw is connected, biassed by another spring, is able to come down against a surface of the jaw mechanism to which no ring handle is connected to close the jaws.

In general the cartridge mechanism of the invention comprises means for holding a stack of generally U-shaped clips aligned perpendicular to the plane of the pusher channel, a spring to push the clips toward the pusher channel, a bottom stop for preventing the clips from falling out of the cartridge, interlocking mechanism for interlocking the cartridge with the instrument, a clip follower between the stack of clips and the spring mechanism, and finger grips for ease of application and removal of the cartridge to or from the instrument. As used herein, U-shaped indicates a clip having two substantially parallel arms connected by a bight of constant radius, by a V-shaped section, or by any variation of these.

The clips are preferably rectangular in cross section and provided with a knurled pattern on the inside surface to help retain tissue. A rectangular cross section having a height/width ratio of 2/1 is particularly preferred to prevent the clips from twisting as they are closed and to provide the closed clip with a square cross section. The clip may be of any convenient size and constructed of any biomedically acceptable material. A particularly preferred clip is one formed of tantalum and having a uniform rectangular cross section of 0.015 in. wide by 0.030 in. high. The inside surface of the clip is preferably coined in a diamond knurl pattern to increase the gripping power of the clip on the tissue.

SPECIFIC DESCRIPTION

More particularly, referring to FIG. 1, a repeating hemostatic clip applying instrument according to the invention is generally indicated at 42. It comprises a left and a right jaws 44 and 46 at the end of left and right distal end portions 48 and 50.

Referring to FIGS. 1 and 8, left jaw 44 is mounted to the distal end 48 of a left jaw actuating member generally indicated at 52 comprising the aforesaid distal end 48, pivot hole 54, handle shaft 56, handle ring 58, and sequencing stop extension 60. Distal end 48 is provided with a cartridge clearance cut out 62 (see also FIGS. 7 and 9). A jaws return spring 64 is attached to the handle shaft 56 by means of appropriate rivets, screws, or the like 66.

Still referring to FIGS. 1 and 8, particularly FIG. 8, the right jaw 46 and right distal extension 50 are part of a single main body generally indicated at 68. Main body 68 has a pivot hole 70, commonly pivoted to pivot hole 54 on left jaws actuating member 52 around a pivot 72 shown in FIG. 1. The main body 68 has a channel formed therein by alternating slots 74 in the bottom thereof and 76 in the top thereof which overlap to form a continuous channel which terminates at an elongated cut out 78 for receiving the cartridge generally indicated at 80.

The pusher channel is extended as clip channel 82 on the bottom side of the distal end 50 of the main body 68 to the right jaw 46.

The main body 68 is also provided with stabilizing flanges 84, bell crank pivot hole 86, a pusher actuating member stop 88, a pusher actuating member pivot 90 to which a pusher actuating member, generally indicated at 92, is pivoted by means of a pivot hole 94 therein, and a pivot 96 (FIG. 1).

Still referring to FIGS. 1 and 8, particularly FIG. 8, the pusher actuating member 92 comprises a handle shaft 96, a ring handle 98, and a bell crank actuator extension 100 having a bell crank pivot slot 102 therein. The pusher actuating member 92 is provided with a pusher return spring 104 which is preferably less strong than the jaws return spring 64.

Still referring to FIGS. 1 and 8, particularly FIG. 8, a clip pusher, generally indicated at 106, is preferably provided with a thin forward portion 108 and thick rearward portion 110. It is connected by means of pivot 112 to a pusher link 114, which in turn is connected by means of a pivot 116 to a bell crank, generally indicated at 118. As best seen in FIG. 1, bell crank 118 is provided at one end with a bifurcated arm 122 straddling a narrow portion of pusher link 114 and at its opposite end with a bifurcated arm 124 straddling bell crank actuator extension 100. Pivot pin 126 is fixed in arm 124 and rides in bell crank pivot slot 102 (FIG. 8).

Still referring to FIGS. 1 and 8, the bell crank 118 is provided with a sequencing stop surface 128 on which sequencing stop extension 60 rides, a sequencing drop-off cut out 130 and a main pivot 132 pivoted to the bell crank pivot hole 86 by means of pivot 134 (FIG. 1) - sequencing stop surface 128 and cut out 130 forming a cam.

The main body 68 is relieved at 95 for rotation of bell crank 118 and at 95' for rotation of the link 114 and rotation of bell crank 118 (FIGS. 1 and 2).

Now referring to FIGS. 9 through 13, a plurality of U-shaped hemostatic clips, generally indicated at 136, are stacked vertically in clip chamber 170 of cartridge 80 formed by guide means 158, 160 and 166. Clip stack 136 is perpendicular to the plane of pusher 106 with lowermost clip 142 resting in the plane of pusher 106 on clip stop platform 162. Platform 162 cooperates with clip chamber guide means to form a rearward aperture for receiving pusher 106 and a forward rectangular slot 169 for passing clip 142 from the cartridge. Clip guide means 152 which also functions as an interlocking mechanism for interlocking the cartridge with the instrument, has a channel corresponding in width to the width of the clips 136 and slot 169 for guiding and aligning clip 142 as it is pushed from the clip stack into clip channel 82 by pusher 106. Lowermost clip 142 resting on platform stop 162, forward slot 169 and the channel in clip guide 152, are all aligned with clip channel 82 extending to jaws 44 and 46 when cartridge 80 is mounted on instrument 42 as best seen in FIG. 9.

In operation, with the cartridge 80 mounted to the instrument 42 as illustrated in FIGS. 1 through 4, the pusher 106 extends to just behind the clips 136. The surgeon places the jaws 44–46 about tissues to be clipped. He then closes the two ring handles 58–98. First the pusher actuating member 92 moves about pivot 97 against pusher return spring 104, this rotates the bell crank counter-clockwise pushing the pusher 106 by means of pusher link 114 to cause the lowermost clip 142 (FIG. 9) in the clip stack 136 to be advanced through slot 169 and the channel of clip guide means 152 into channel 82 to between the jaws 44 and 46 as shown in FIG. 3. Since the jaws 44–46 surround tissue, the clip 142 is pushed around the tissue and remains in the jaws. As shown in FIGS. 5 and 7, the jaws 44–46 are preferably provided with clip slots 138 extending from the clip channel 82 and opening at a two degree angle therefrom. This angle assures that the jaws will be parallel when closed. Small detents (not shown) may be disposed at the forwardmost end of the clip slots 138 (FIG. 7) to stop distal motion of the clip.

During the above action, and referring to FIG. 3, the sequencing stop extension 60 has been riding on the sequencing stop surface 128 of the bell crank 118. However, once the pusher 106 has advanced to its farthest position (at this position pusher actuating member handle shaft 96 contorts stop 88), the sequencing stop extension 60 drops into the sequencing drop cutoff 130 on the bell crank 118. This allows the left jaw actuating member 52 to rotate about pivot pin 72 thereby bringing the left jaw 44 against the right jaw 46, to close the clip 142 all as shown in FIG. 4. The sequencing drop cutoff 130 positively prevents return of the pusher 106 so that the clip is positively locked between tissue, jaws 44–46, and the distal end of the pusher 106 until the jaws are closed.

When the surgeon now releases the pressure on the handle shafts 56 and 96 of the left jaw actuating member 52 and pusher actuating member 92, the jaw return spring 64 first rotates left jaw actuating member 52 about pivot pin 72 under action of the jaws return spring 64 until it comes against the head of adjustment screw 144 mounted to the main body 68. Cam surface 130, being released by stop extension 60, rotates about pivot 134 and pusher actuating member 92, under the action of pusher return spring 104, rotates about pivot 97 returning the instrument to its rest position shown in FIG. 2.

The clips may also be mounted in the cartridge 80 with their open ends slightly resiliently pressed together so that they tend to widen when released. This allows them to widen when they reach the jaws 44–46 and to be resiliently retained therein. Alternatively, the clearance between the jaws may be made smaller than the channel through which the clips are pushed, so that they are resiliently squeezed down when they reach the jaws to be retained therein. The clip slots may also be provided with transversely oriented serrations for retaining the clips therein, in the manner disclosed in U.S. Pat. No. 3,713,533.

Again, referring to FIGS. 9 through 13, the cartridge 80 comprises a main body portion 146, preferably of transparent plastic material for low cost manufacture and to allow the user to see the number of clips 136 remaining in the stack or magazine and a leaf spring 148 mounted thereto, by suitable attachment means, for example, a screw 150. Those skilled in the art will understand that spring 148 may be attached by means of a heat sealed plastic rivet or might even be integrally molded with the body 146 if a suitable plastic were employed. The cartridge 80 fits snugly into cartridge cut out 78 in right jaw extension 50. The forward end of the cartridge body 146 is provided with a forward clip guide means and retention tongue 152. Since the cartridge closely fits into the cut out 78, no other retention means is required. However, a detent and recess may be provided at the rear extension 154 of the cartridge body 146 and the rear end 156 of the cut out 78, or on other suitable parts of the cartridge and adjacent parts of the instrument.

The cartridge body is provided with guide surfaces 158 and 160 for guiding the clip magazine or stack 136 and at the bottom thereof with a clip platform stop 162, which fits into the cartridge clearance cut out 62 in the distal left jaw extension 48. The end of the spring 164 preferably extends through a cut out 166 to provide a visual indication of the number of clips remaining in the stack 136.

Spring pressure and friction prevents bottom clip 142 from moving either forward or rearward when the cartridge is out of the instrument. A clip follower 172 is provided for applying the force of the spring 148 against the clip stack 136 in an even manner. To this end, the clip follower 172 is provided with a clip follower fulcrum ridge 174 within a clip follower spring guide slot generally indicated at 176. Since the clip follower fulcrum ridge 174 is at the middle of the clip follower 172, the force is applied evenly to the clip stack 136 and the clips stack cannot rock out of alignment with the clip channel extension 82.

An alternative form sequencing mechanism is employed in the alternative embodiment illustrated in FIGS. 15, 16, and 17. Here, the bell crank, generally indicated at 180, is provided with a sequencing stop extension accepting slot 182 for receiving an elongated sequencing stop extension 184 mounted to the handle shaft 56 of the left jaw actuating member generally indicated at 52. The pusher slide channel 186 is formed in two pieces, 188 and 190, joined together by a plurality of fasteners 192. A single spring 194 is employed which is mounted to handle 56 by rivets or screws 196 and acts between handle 56 and bell crank actuator extension 100 by means of ears 198 acting on extended pivot pin 200.

Referring to FIG. 17 in this embodiment of the invention, the bell crank 180 is provided with a narrow arm 202 which fits into a slot 204 formed in the bell crank actuator extension 100.

In another alternative form of the invention, illustrated in FIG. 18, the thin forward portion 108 of the clip pusher 106 (not shown) is made flexible and the distal extensions 50 and 48 are curved for better visibility of the tip for use by surgeons who are used to curved or offset hemostatic instruments. The cartridge 80 may be, but need not be, conformed to this curvature which may be restricted to the portion of the instrument between the jaws 44 and 46 and the rearward end of the cartridge 80.

Now referring to FIG. 8, those skilled in the art will understand, upon reflection, that the two pivot points of pivot holes 54 and 70 and pivot holes 90 and 94 respectively, could be combined into common axis. That is, pivot hole 70 could be eliminated and pivot hole 54 moved down until it was in line with pivot holes 90 and 94 when the instrument was assembled. Furthermore, the cartridge cut out 50 and main body 68 could be formed as part of the left jaws actuating member in which case the right jaws actuating member would comprise only the right jaw 46, the distal extension 50, the pivot hole 90, and the pusher actuating member stop 88, which also acts as the right jaws actuating member when contacted by the handle shaft 96 of the pusher actuating member 92.

Now referring to FIG. 19, a single pivot instrument is generally indicated at 220. It comprises a main body 222 having a jaws extension 224 terminating in lower jaw 226. The upper finger loop extension 228 is integral with the main body 222 and terminates in upper finger loop 230. Lower finger loop extension 232 is pivoted to the main body at pivot 234 and terminates in lower finger loop 236. Upper jaw 238 is mounted to an arm also pivoted at pivot 234 and terminating at an asymmetrical T-shaped extension generally indicated at 240. The lowermost extension 242 is contacted with lower finger loop extension 232 when the two finger loops 230 and 236 are brought together and this causes the T-shape extension 240 and the upper jaw 238 to pivot about pivot 234 against the action of a spring 244 mounted at one end to finger loop extension 228 and engaging the uppermost portion 246 of the T-shaped extension 240.

The pusher mechanism is mounted in the main body 222 and a portion of the pusher channel 248 may be seen. The distal end of the pusher 250 is pivoted at pivot 252 to link 254. Link 254 is pivoted at pivot 256 to floating bell crank 258 which is pivoted at pivot 260 and connected at its other end at pivot 262 to lowermost finger loop extension 232. Pivot 260 is connected to link 264 which in turn is connected at its other end at pivot 266 to spring 265 which may be integral with spring 244 both being mounted to uppermost finger loop extension 228. Travel of spring 265 is preferably limited by stop 268 integrally formed with uppermost finger loop extension 228.

When the two finger loops 230 and 236 are brought together pivot 260 moves to position 260' and the linkages and other pivots move to the positions shown by the dotted lines and circles connected to point 260'. This causes the pusher to move fully forward pushing the clip from the cartridge 269 forward in between the jaws 226 and 238. As the front end of finger loops 230 and 236 are brought closer together, pivot 266 moves to point 266' and lowermost finger loop extension 232 moves to position 232' shown by dotted lines thus engaging the T-extension 240 and closing the uppermost jaw 238 against the lower jaw 226.

Now referring to FIG. 20, an alternative form of clip cartridge 270 having clipstack 272 therein may be provided with an internal clip leg or with supporting flanges 274 to prevent the clips 272 from bending inward within the cartridge 270. It will be understood that the walls of the cartridge 276 and 278 which engage the back bight 280 of the clipstack 272 need not continue all the way around the clips but merely need to engage the back of the clips to prevent them from moving backward in the stack.

In FIG. 21 there is shown a preferred form of U-shaped clip 300 having straight legs 302 and a V-shaped bight 304. The apex 306 of the bight 304 provides a crease which insures that the clip will close at the apex. This provides smoother operation of the instrument and insures that the legs 302, when closed on a bleeder, are of the same length. Otherwise, clip 300 is the same as those previously described.

Referring again to FIGS. 1 through 4, those skilled in the art will also understand that the pusher return spring 104 acting between the main body 68 and the pusher actuating member 92, could be located anywhere in the operating chain between the bell crank actuator extension, the bell crank 118, the pusher link 114 or the clip pusher 106, and the main body 68. All that is required is that a force cause the pusher member 106 to return to its normal position. This will also cause the entire mechanism including the pusher actuating member 92 to return to its normal rest position. Thus a compression spring may be located within the main body operating directly on the pusher 106 or the link pin 112 or a coil spring may operate between the main body 68 and the bell crank 118, or between the bell crank and the pusher link, or between the bell crank and the bell actuator extension. Similarly, the jaws return spring 64 may be replaced by any spring providing ultimately a rotational force between the left jaw actuating member 52 and the right jaw 46. Thus, compression springs may be mounted between the main body 68 and the handle shaft 56 or between the distal extension 48 and 50, or a coil spring may act at the pivot hole or at the pivot 72 (FIG. 1). Similarly, a coil spring acting at the pivot 97, between the main body 68 and the pusher actuating member 92 could replace the pusher return spring 104.

Those skilled in the art will also understand that many different sequencing mechanisms could be employed, which, upon bringing the two ring handles 58 and 98 together, would cause the pusher 106 to advance the lowermost clip 142, and then the jaws 44 and 46 to close, closing the clip. One such instrument employing a free floating bell crank is illustrated in FIG. 19. This instrument also employs a single pivot. Now referring to FIG. 19, many other sequencing mechanisms will come to mind, for example, a rack and gear mechanism for advancing the pusher. However, it will be noted by those skilled in the art that I have provided simple mechanisms employing only rotary contacts for low friction and smooth operation, which also provide very long pusher travel for relatively small closure travel between the ring handles.

I have thus provided repeating clip applying instruments and cartridges therefor, which may be employed during an operation to apply any number of hemostatic clips by merely changing pre-sterilized cartridges containing a plurality of the clips.

It will thus be seen that the objects set forth above, among those made apparent from the preceding description, are efficiently attained and since certain changes may be made in the above articles and constructions without departing from the scope of the invention, it is intended that all matter contained in the above description or shown in the accompanying drawings shall be interpreted as illustrative and not in a limiting sense.

For example, all of the clips in the cartridge need not be stacked as I have shown in FIG. 9. All that is necessary is that the bottom most clip 142 be presented at the end of the pusher and the beginning of the clip channel leading to the jaws. Thus, the clips might be mounted horizontally in a plane above the pusher, all biased by a spring forward, and another spring would be provided for biasing the forwardmost clip downward against the clip platform stop so that it would be in position at the forward end of the pusher for being pushed into the clip channel. Many other variations will readily come to mind upon reflection.

Moreover, it will be seen that I have provided a repeating hemostatic clip applying instrument involving very few parts, which is simple to operate and use, convenient to sterilize and surprisingly provides this in an instrument which handles in the manner in which surgeons have desired for many years. I have achieved this surprising result by a cunning choice of elements that synergistically work together.

It is to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A hemostatic clip cartridge adapted to be removably mounted on a repeating hemostatic clip applying instrument, said cartridge comprising:
  A. a plurality of generally U-shaped planar hemostatic clips in vertical alignment forming a U-shaped stack, said clips adapted to be crushed about tissue one at a time by the instrument;
  B. stack-guide means for confining and guiding said U-shaped stack for motion along the vertical axis of said stack;
  C. spring means for biasing said stack downward;
  D. stop means at the bottom of said stack-guide means for preventing said stack from further downward motion, said stop means cooperating with said stack-guide means to form a rearward aperture for receiving a clip pusher member of the instrument and a forward rectangular slot for passing a single clip;
  E. clip-guide means comprising a channel member extending horizontally from said forward slot, the width of said forward slot corresponding to the width of the channel in said clip-guide means; and,
  F. quick release interlocking means adapted to interlock with the instrument for quickly mounting and dismounting the cartridge on the instrument so that a plurality of cartridges can be used in a single surgical procedure;

wherein said clip pusher member of the instrument upon which the cartridge is mounted may push the lowermost clip of said stack through said forward slot and into said clip-guide means.

2. The cartridge of claim 1 wherein said planar clips are of substantially uniform rectangular planar cross section.

3. The cartridge of claim 2 wherein the ratio of height to width of the rectangular cross section of each clip is approximately 2:1.

4. The cartridge of claim 1 wherein said U-shaped planar clips comprise two substantially parallel arms connected by a bight of constant radius.

5. The cartridge of claim 1 wherein said U-shaped planar clips comprise two substantially parallel arms connected by a V-shaped section.

6. The cartridge of claim 1 wherein the inner surface of said U-shaped clips is roughened relative to the outer suface.

7. The cartridge of claim 6 wherein the said inner surface of said clips is coined in a diamond shaped, knurled pattern.

8. The cartridge of claim 1 wherein said stop means comprises a plate across the bottom of said guide means.

9. The cartridge of claim 1 wherein the channel member of said clip-guide means has an open bottom.

10. A hemostatic clip cartridge adapted to be removably mounted on a repeating hemostatic clip applying instrument, said cartridge comprising:
A. a plurality of generally U-shaped planar hemostatic clips in vertical alignment forming a U-shaped stack, said clips adapted to be crushed about tissue one at a time by the instrument;
B. a clip follower bearing on the uppermost clip in said stack and having an outside dimension corresponding to the dimensions of said U-shaped stack;
C. stack-guide means for confining and guiding said clip follower and U-shaped stack for motion along the vertical axis of said stack;
D. spring means for biasing said clip follower and said stack downward;
E. stop means at the bottom of said stack-guide means for preventing said stack from further downward motion, said stop means cooperating with said stack-guide means to from a rearward aperture for receiving a clip pusher member of the instrument and a forward rectangular slot for passing a single clip;
F. clip-guide means comprising a channel member extending horizontally from said forward slot, the width of said forward slot corresponding to the width of the channel in said clip-guide means; and
G. quick release interlocking means adapted to interlock with the instrument for quickly mounting and dismounting the cartridge on the instrument so that a plurality of cartridges can be used in a single surgical procedure;
whereby said clip pusher member of the instrument upon which the cartridge is mounted may push the lowermost clip of said stack through said forward slot and into said clip-guide means.

11. The cartridge of claim 10 wherein said clip follower has a planar surface bearing on the uppermost clip of said stack and a fulcrum contacting said spring means.

12. The cartridge of claim 11 wherein said fulcrum comprises a ridge extending across the center of said clip follower.

13. The cartridge of claim 10 and
G. an elongated cartridge body in which said stop means, said stack-guide means, said rearward aperture and said forward rectangular slot are formed; and
wherein said spring comprises an elongated spring attached to the rear of said cartridge body.

14. A clip supply cartridge removably mountable upon a repeating clip applying surgical instrument having an axial clip channel and a narrow elongated clip pusher for pushing a clip through said channel to a pair of jaws, said instrument adapted to permit removal of a plurality of clips from the cartridge by the instrument one at a time with each actuation of the instrument, said cartridge comprising:
A. a chamber adapted to confine a stack of generally U-shaped clips and permit motion of the stack only along its axis, having guide means parallel to the stack of clips, said clips adapted to be crushed about tissue one at a time by the instrument;
B. stop means at one end of the chamber to prevent the clips from escaping from the chamber along the axis of the chamber;
C. spring means urging an entire stack of clips contained within said chamber against said stop means;
D. two openings in the chamber adjacent to the stop means permitting only the one clip in contact with the stop means to pass through by moving in a direction parallel to the arms of the U-shaped clip in a plane at substantially right angles to the axis of the clip stack, said openings providing a passageway through which the narrow elongated clip pusher of the instrument may move to force a clip out of the cartridge and into a channel in the instrument;
E. means for aligning and retaining the cartridge on the instrument such that the clip in the cartridge in contact with the stop means is aligned with the channel of the instrument and as the pusher forces the clip all the way to the jaws of the instrument the remaining clips in the cartridge are blocked by the pusher from entering the position adjacent to the stop means; and
F. quick release interlocking means adapted to interlock with the instrument for quickly mounting and dismounting the cartridge on the instrument so that a plurality of cartridges can be used in a single surgical procedure.

15. The cartridge defined in claim 14 wherein said alignment and retention means comprises a tongue extending from the vicinity of the opening from which clips are ejected one at a time, said tongue having a slot through which the clips and the pusher of the instrument may pass and being adapted to slip snugly beneath an undercut on the instrument.

16. The cartridge defined in claim 14 wherein said spring means comprises a leaf spring.

17. The cartridge defined in claim 16 and
F. a clip follower for use within said clip chamber adapted to be placed between the stack of clips and said leaf spring acting on the stack of clips, said clip follower having a shape in cross section substantially the same as the cross section of said clip chamber and having a ridge forming a fulcrum upon which said leaf spring rides so as to distribute the force uniformly to the clip stack throughout the range of motion of said leaf spring.

18. A clip follower as defined in claim 17 having a verticle dimension large enough that it cannot be ejected from the opening in the cartridge that the clips are ejected from and serving to lock the instrument when the cartridge is empty.

19. The cartridge defined in claim 14 wherein said chamber has means for retaining each arm of the clips from two sides.

20. The cartridge defined in claim 14 having two finger grips which project beyond the edges of the instrument when the cartridge is mounted thereupon to facilitate mounting the cartridge to and removing the cartridge from the instrument.

21. A hemostatic clip magazine adapted to be removably mounted on a repeating hemostatic clip applying instrument, said cartridge comprising a plurality of identical planar hemostatic clips of substantially uniform rectangular planar cross-section, said clips adapted to be crushed flat about tissue one at a time by the instrument, formed of elongated material of rectangular cross-section into a generally U-shape, and comprising two parallel straight portions connected by a bight, the dimensions of said rectangular cross-section throughout a substantial portion of said straight portions being substantially two to one with the shorter dimension take parallel to the plane formed by said straight portions, a diamond shaped knurled pattern coined in the entire inner surface of said U-shaped clips, and said U-shaped clips being stacked in vertical alignment to form a U-shaped stack and quick release interlocking means adapted to interlock with the instrument for quickly mounting and dismounting the cartridge on the instrument so that a plurality of cartridges can be used in a single surgical procedure.

22. The hemostatic clip magazine defined in claim 21 wherein said bight portion is of substantially constant radius.

23. The cartridge of claim 1 wherein said clips are adapted to be crushed flat about tissue.

24. A hemostatic clip cartridge comprising:
  a. a plurality of generally U-shaped planar hemostatic clips in vertical alignment forming a U-shaped stack, said clips adapted to be crushed flat about tissue one at a time by the instrument;
  b. stack-guide means for confining and guiding said U-shaped stack for motion along the vertical axis of said stack;
  c. spring means for biasing said stack downward;
  d. stop means at the bottom of said stack-guide means for preventing said stack from further downward motion, said stop means cooperating with said stack-guide means to form a rearward aperture for receiving a clip pusher member of the instrument and a forward rectangular slot for passing a single clip;
  e. clip-guide means comprising a channel member extending horizontally from said forward slot, the width of said forward slot corresponding to the width of the channel in said clip-guide means;
  whereby said clip pusher member may push the lowermost clip of said stack through said forward slot and into said clip-guide means.

25. The cartridge defined in claim 14 and
  F. a clip follower for use within said clip chamber adapted to be placed between the stack of clips and said spring acting on the stack of clips, said clip follower having a shape in cross section substantially the same as the cross section of said clip chamber and having a ridge forming a fulcrum upon which said spring rides so as to distribute the force uniformly to the clip stack throughout the range of motion of said spring.

26. The cartridge defined in claim 25 having an elongated opening through which a free end of said spring projects beyond said chamber without permitting escape of the clips, such that the position of the free end of said spring is visible when the cartridge is mounted upon the instrument and its position provides an estimate of the number of clips remaining in the cartridge.

* * * * *